US012577192B2

(12) United States Patent
Jung et al.

(10) Patent No.: US 12,577,192 B2
(45) Date of Patent: Mar. 17, 2026

(54) PROCESS FOR HYDROGENATION OF PHTHALATE BASED COMPOUND

(71) Applicant: HANWHA SOLUTIONS CORPORATION, Seoul (KR)

(72) Inventors: Kitaeg Jung, Daejeon (KR); Hyo Suk Kim, Daejeon (KR); Seongmin Park, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 964 days.

(21) Appl. No.: 17/770,611

(22) PCT Filed: Oct. 27, 2020

(86) PCT No.: PCT/KR2020/014695

§ 371 (c)(1),
(2) Date: Apr. 20, 2022

(87) PCT Pub. No.: WO2021/096103

PCT Pub. Date: May 20, 2021

(65) Prior Publication Data

US 2022/0388940 A1 Dec. 8, 2022

(30) Foreign Application Priority Data

Nov. 15, 2019 (KR) ........................ 10-2019-0146796

(51) Int. Cl.
*C07C 67/303* (2006.01)
*C07C 69/75* (2006.01)
*C08K 5/12* (2006.01)

(52) U.S. Cl.
CPC ............ *C07C 67/303* (2013.01); *C07C 69/75* (2013.01); *C08K 5/12* (2013.01); *C07C 2601/14* (2017.05)

(58) Field of Classification Search
CPC .......... C07C 67/303; C07C 69/75; C08K 5/12
See application file for complete search history.

(56) References Cited

U.S. PATENT DOCUMENTS 8,946,467 B2 2/2015 Reine
2002/0019559 A1* 2/2002 Brunner ................ C07C 67/303 560/55
2018/0163019 A1* 6/2018 Kim ........................ C07C 69/80

FOREIGN PATENT DOCUMENTS

CN 1835908 A 9/2006
CN 101522301 A 9/2009
(Continued)

OTHER PUBLICATIONS

Third Party Observation of EP Patent Application No. 20887046.9.
Hexamoll DINCH, BASF Technical Information, (Jul. 1, 2019).
Palatinol N, BASF Technical Information, (Jul. 1, 2019).

*Primary Examiner* — John E Uselding
(74) *Attorney, Agent, or Firm* — Harvest IP Law, LLP

(57) ABSTRACT

This invention relates to a process for hydrogenation of a phthalate based compound. According to the invention, generation of by-products is inhibited during hydrogenation, and thus, catalytic activity is improved and life is prolonged, thereby increasing efficiency and economical feasibility of the industrial process. And, since the hydrogenation product prepared according to the invention has high purity and low acid value, it has excellent qualities as a plasticizer, and thus, can be used for various products.

11 Claims, 1 Drawing Sheet

(56) References Cited

FOREIGN PATENT DOCUMENTS

| | | | |
|---|---|---|---|
| CN | 102958900 | A | 3/2013 |
| CN | 107043325 | A | 8/2017 |
| DE | 19721347 | A1 | 11/1998 |
| EP | 1042273 | B1 | 5/2003 |
| EP | 3293172 | A2 | 3/2018 |
| JP | 2001089776 | A | 4/2001 |
| JP | 2007504105 | A | 3/2007 |
| JP | 2017137285 | A | 8/2017 |
| JP | 2018504268 | A | 2/2018 |
| KR | 100284475 | B1 | 4/2001 |
| KR | 20010033257 | A | 4/2001 |
| KR | 1020060118423 | A | 11/2006 |
| KR | 1020090037902 | A | 4/2009 |
| KR | 1020090038514 | A | 4/2009 |
| KR | 101556340 | B1 | 9/2015 |
| KR | 20170121058 | A | 11/2017 |
| KR | 2019-0063106 | A | 6/2019 |
| KR | 1020190063104 | A | 6/2019 |
| WO | 9932427 | A1 | 7/1999 |
| WO | 2019107770 | A1 | 6/2019 |

* cited by examiner

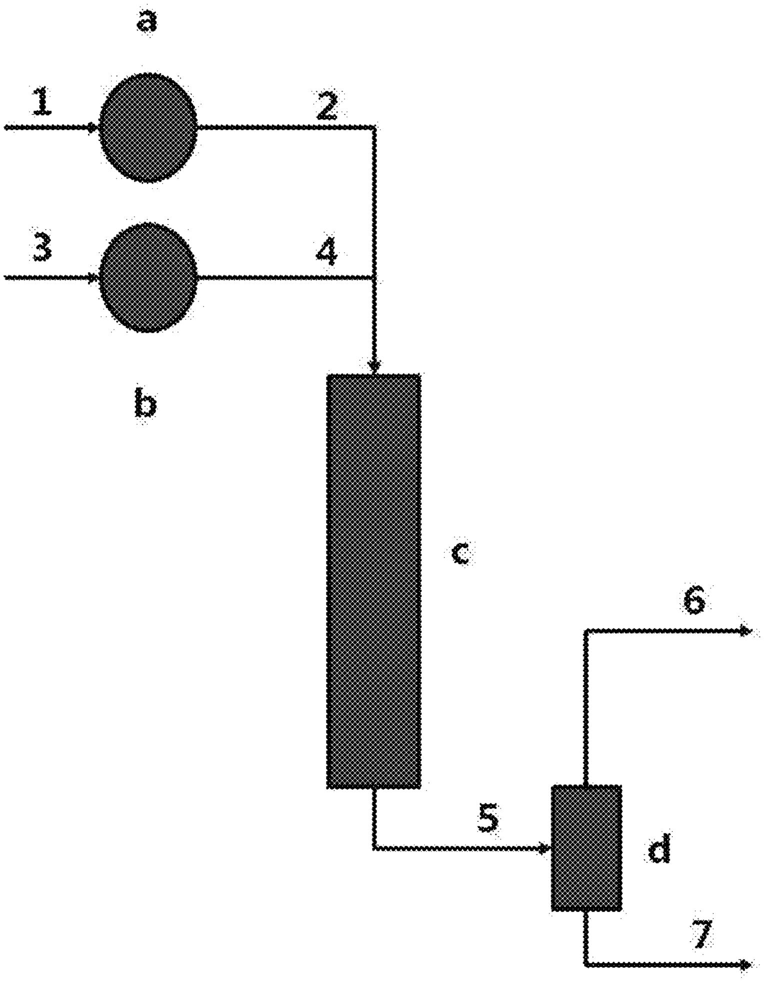
a
1
2
3
4
b
c
6
5
d
7

PROCESS FOR HYDROGENATION OF PHTHALATE BASED COMPOUND

CROSS REFERENCE TO RELATED APPLICATION(S)

This application is a National Stage of International Application No. PCT/KR2020/014695 filed on Oct. 27, 2020 claiming the benefit of Korean Patent Application No. 10-2019-0146796 filed on Nov. 15, 2019 with the Korean Intellectual Property Office, the disclosures of which are herein incorporated by reference in their entirety.

This invention relates to a process for hydrogenation of a phthalate based compound. Specifically, this invention relates to a process for hydrogenation of a phthalate based compound that conducts hydrogenation while decreasing the content of impurities in the reactants used during hydrogenation of a phthalate based compound, and thus, can inhibit generation of by-products and prolong catalyst life, and can improve quality as a plasticizer by maintaining acid value of the hydrogenation product low.

BACKGROUND ART

A phthalate based compound is material widely used as a plasticizer of plastic, particularly polyvinyl chloride (PVC). For example, it has a variety of uses including electric and electronic products, medicine, paint pigment, lubricant, binder, surfactant, adhesive, tiles, food containers, packaging material, and the like.

However, as some phthalate based compounds are known to cause environmental pollution and human endocrine disruption, regulation of the use is being strengthened around advanced countries such as Europe, the US, and the like. Particularly, among phthalate based plasticizers, some products such as di(2-ethylhexyl) phthalate (DEHP)), butyl benzyl phthalate (BBP), di-n-butyl phthalate (DBP) are suspected as endocrine disruptors disturbing or confusing the action of human hormone, and thus, there is movement to regulate the same.

Thus, there are many efforts to develop environmentally friendly plasticizers that exhibit equivalent performance to the existing plasticizers, and are free of environmental hormone issue, and as one of them, there is a method of using compounds wherein a benzene ring included in phthalate is hydrogenated.

As hydrogenation of an aromatic compound such as a benzene ring, a method of using a catalyst comprising transition metal such as ruthenium as an active ingredient in a support (carrier) is known.

However, the activity of the transition metal catalyst rapidly decreases with the progression of a reaction, thus causing decrease in yield. Thus, there are continued efforts to solve the problem of hydrogenation so as to improve productivity and economical efficiency of the process. For example, Korean Registered Patent No. 1556340 suggests a hydrogenation process in which phthalate is reacted with hydrogen in the presence of a hydrogenation catalyst and alcohol, and discloses that catalyst performance and life may be improved according to the process.

Meanwhile, the hydrogenation involves side reactions, and as the content of by-products increases, the prepared product becomes acidic, and if acid value of the product exceeds a certain level, odor may be generated, purity may decrease, and thus, quality problem as a plasticizer may be generated. Moreover, since the by-products also decreases the activity of a hydrogenation catalyst, in order to improve productivity and economical efficiency of the process and improve quality of the product, there is a demand for novel hydrogenation process of phthalate based compounds capable of inhibiting generation of by-products.

PRIOR ART DOCUMENT

Patent Document (Patent Document 1) Korean Registered Patent No. 1556340, “A process for hydrogenation of a phthalate based compound”

DETAILED DESCRIPTION OF THE INVENTION

Technical Problem

It is an object of the invention to provide a process for hydrogenation of a phthalate based compound wherein by decreasing the content of impurities in the reactants used during hydrogenation of a phthalate based compound, by-products generated by side reactions of the impurities is decreased, and thus, acid value increase in the final product due to the by-products is inhibited, and inactivation speed of the catalyst due to the acidic material is lowered, thereby prolonging catalyst life, and acid value of the hydrogenation product is maintained low, thereby improving quality as a plasticizer.

Technical Solution

In order to solve the problem, there is provided a process for hydrogenation of a phthalate based compound comprising steps of introducing gas-phase raw material including hydrogen; and liquid-phase raw material including a phthalate based compound into a reactor, and conducting hydrogenation of the hydrogen and phthalate based compound in the presence of a hydrogenation catalyst, wherein HAZE value of the liquid-phase raw material is 8% or less, and acid value of the hydrogenation product separated after the hydrogenation is 0.3 KOHmg/g or less.

In the hydrogenation process of the phthalate based compound, HAZE value of the liquid-phase raw material may be preferably 6% or less, or 4% or less.

And, acid value of the hydrogenation product separated after the reaction may be 0.15 KOHmg/g or less, or 0.07 KOHmg/g or less.

And, acid value after heating of the reaction product separated after the reaction may be 0.4 KOHmg/g or less, or 0.25 KOHmg/g or less, or 0.15 KOHmg/g or less.

And, the amount of hydrogen introduced into the reactor may be 3 to 300 moles, or 3 to 30 moles, based on 1 mole of the phthalate based compound.

And, the phthalate based compound may comprise phthalate, terephthalate, isophthalate, or carboxylic acid derivatives or mixtures thereof, and more specifically, the phthalate based compound may be phthalate or terephthalate.

And, the gas-phase raw material may be fed from the upper part or lower part of the reactor, and the liquid-phase raw material may be fed from the upper part of the reactor.

And, the hydrogenation catalyst may comprise one or more active ingredients selected from the group consisting of ruthenium (Ru), rhodium (Rh), palladium (Pd), and platinum (Pt).

And, the hydrogenation catalyst may further comprise a carrier, wherein the active ingredients may be included in an amount of 3 parts by weight or less, based on 100 parts by weight of the carrier.

And, the process for hydrogenation of a phthalate based compound may further comprise a step of filtering the liquid-phase raw material using a filter at a temperature of 150° C. or less, before introducing the liquid-phase raw material.

And, the process for hydrogenation of a phthalate based compound may further comprise a step of introducing one or more of a neutralization agent and water into the liquid-phase raw material and mixing them, before the filtering.

And, the process for hydrogenation of a phthalate based compound may further comprise a step of stripping the liquid-phase raw material, before the filtering.

According to the invention, there is also provided a hydrogenated phthalate based compound, prepared by the process for hydrogenation of a phthalate based compound.

The hydrogenated phthalate based compound may be hydrogenated phthalate or hydrogenated terephthalate.

According to the invention, there is also provided a plasticizer comprising the hydrogenated phthalate based compound.

According to the invention, there is also provided a resin composition comprising the plasticizer; and one or more kinds of resin selected from the group consisting of ethylene vinyl acetate, polyethylene, polypropylene, polyvinyl chloride, polystyrene, polyurethane, polybutadiene, silicon, thermoplastic elastomer and copolymers thereof.

Advantageous Effects

According to the process for hydrogenation of a phthalate based compound of the invention, generation of by-products is inhibited, and thus, catalytic activity is improved and life is prolonged, thereby increasing efficiency and economical feasibility of the industrial process. And, the hydrogenation product prepared according to the invention has high purity and low acid value, and thus, has excellent quality as a plasticizer, and thus, can be applied for various products.

BRIEF DESCRIPTION OF THE DRAWINGS

FIG. 1 is a schematic diagram showing the hydrogenation apparatus used in the hydrogenation process of the invention.

REFERENCE NUMERALS a, b: heat exchanger
c: reactor
d: gas-liquid separator
1: gas-phase raw material, 2: temperature raised gas-phase raw material
3: liquid-phase raw material, 4: temperature raised liquid-phase raw material
5: reaction mixture
6: gas-phase unreacted material
7: liquid-phase reaction product

DETAILED DESCRIPTION OF THE EMBODIMENTS

Although various modifications can be made to the invention and the invention may have various forms, specific examples will be illustrated and explained in detail below. However, it should be understood that these are not intended to limit the invention to specific disclosure, and that the invention includes all the modifications, equivalents or replacements thereof without departing from the spirit and technical scope of the invention. And, in case it is judged that specific explanations about related known technology may obscure the subject of the invention, detailed explanations thereof will be omitted.

As used herein, terms including ordinal numbers such as first, second, and the like may be used to explain various constructional elements, but the constructional elements are not limited thereby. These terms are used only to distinguish one constructional element from other constructional elements. For example, a first constructional element may be named as a second constructional element without departing from the scope of the right of the invention, and similarly, a second constructional element may be named as a first constructional element.

A singular expression includes a plural expression thereof, unless it is expressly stated or obvious from the context that such is not intended. As used herein, the terms “comprise” or “have”, etc. are intended to designate the existence of practiced characteristic, number, step, constructional element or combinations thereof, and they are not intended to preclude the possibility of existence or addition of one or more other characteristics, numbers, steps, constructional elements or combinations thereof.

Hereinafter, a process for hydrogenation of a phthalate based compound of the invention will be explained in detail with reference to drawings.

According to one embodiment of the invention, there is provided a process for hydrogenation of a phthalate based compound comprising steps of introducing gas-phase raw material including hydrogen; and liquid-phase raw material including a phthalate based compound into a reactor, and conducting hydrogenation of the hydrogen and phthalate based compound in the presence of a hydrogenation catalyst, wherein HAZE value of the liquid-phase raw material is 8% or less, and acid value of the hydrogenation product separated after the hydrogenation is 0.3 KOHmg/g or less.

In the present disclosure, the existence and content of impurities included in the liquid-phase raw material used during hydrogenation of a phthalate based compound are analyzed by HAZE, and by conducting hydrogenation while controlling HAZE of the liquid-phase raw material below a certain level, by-products generated by side reactions of the impurities may be decreased, and thus, increase in acid value in the final product due to the by-products may be inhibited. And, by lowering the inactivation speed of a catalyst due to acidic materials, catalyst life may be prolonged. And, according to the process for hydrogenation of the invention, since the hydrogen product is prepared with an acid value below a certain level, the quality as a plasticizer may be improved.

The reaction subject of the hydrogenation process of the invention is a phthalate based compound comprising benzene-dicarboxylic acid ester or carboxylic acid derivatives thereof. By hydrogenation of the phthalate based compound, hydrogen is added to the benzene ring in the phthalate based compound, and thus, it is converted into corresponding cyclohexane dicarboxylate.

The phthalate based compound may be one or more selected from specifically phthalates, terephthalates, isophthalates and carboxylic acid derivatives thereof. The carboxylic acid derivatives include carboxylic acid, acid anhydride or acid chloride, and the like.

More specifically, the phthalate based compound may be a compound represented by the following Chemical Formula 1:

[Chemical Formula 1]

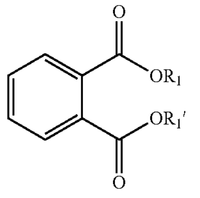

In the Chemical Formula 1, $R_1$ and $R_1'$ are identical to or different from each other, and each independently, hydrogen; or linear or branched alkyl having a carbon number of 1 to 20, specifically 4 to 20, more specifically 5 to 20, or 5 to 10.

And, the phthalate based compound may be ester of phthalic anhydride, wherein in the Chemical Formula 1, $R_1$ and $R_1'$ are each independently, hydrogen; or linear or branched alkyl having a carbon number of 1 to 20, specifically 4 to 20, more specifically 5 to 20, or 5 to 10, provided that at least one of $R_1$ and $R_1'$ is linear or branched alkyl having a carbon number of 1 to 20, specifically 4 to 20, more specifically 5 to 20, or 5 to 10.

As specific examples of the phthalate, dibutyl phthalate (DBP), dihexyl phthalate (DHP), dioctyl phthalate (DOP), di-n-octyl phthalate (DnOP), diisononyl phthalate, or diisodecyl phthalate (DIDP), and the like may be mentioned, but it is not limited thereto. These compounds may be used alone or in combinations.

And, the phthalate based compound may be a compound represented by the following Chemical Formula 2:

[Chemical Formula 2]

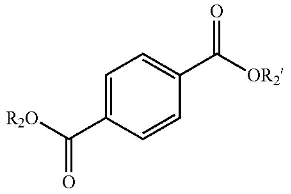

In the Chemical Formula 2, $R_2$ and $R_2'$ are identical to or different from each other, and each independently, hydrogen; or linear or branched alkyl having a carbon number of 1 to 20, specifically 4 to 20, more specifically 5 to 20, or 5 to 10.

And, the phthalate based compound may be ester of terephthalate, wherein in the Chemical Formula 2, $R_2$ and $R_2'$ are each independently, hydrogen; or linear or branched alkyl having a carbon number of 1 to 20, specifically 4 to 20, more specifically 5 to 20, or 5 to 10, provided that at least one of $R_2$ and $R_2'$ is linear or branched alkyl having a carbon number of 1 to 20, specifically 4 to 20, more specifically 5 to 20, or 5 to 10.

As specific examples of the terephthalate, dibutyl terephthalate (DBTP), dioctyl terephthalate (DOTP), diisononyl terephthalate (DINTP), or diisodecyl terephthalate (DIDTP) may be mentioned, but it is not limited thereto. These compounds may be used alone or in combinations.

And, the phthalate based compound may be a compound represented by the following Chemical Formula 3:

[Chemical Formula 3]

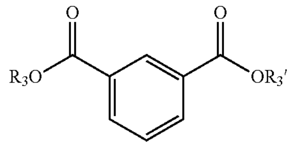

In the Chemical Formula 3, $R_3$ and $R_3'$ are identical to or different from each other, and each independently, hydrogen; or linear or branched alkyl having a carbon number of 1 to 20, specifically 4 to 20, more specifically 5 to 20, or 5 to 10.

And, the phthalate based compound may be ester of isophthalate, wherein in the Chemical Formula 3, $R_3$ and $R_3'$ are each independently, hydrogen; or linear or branched alkyl having a carbon number of 1 to 20, specifically 4 to 20, more specifically 5 to 20, or 5 to 10, provided that at least one of $R_3$ and $R_3'$ is linear or branched alkyl having a carbon number of 1 to 20, specifically 4 to 20, more specifically 5 to 20, or 5 to 10.

As specific examples of the isophthalate, dibutyl isophthalate (DBIP), dioctyl isophthalate (DOIP), diisononyl isophthalate (DINIP), or diisodecyl isophthalate (DIDIP), and the like may be mentioned, but it is not limited thereto. These compounds may be used alone or in combinations.

Among the above phthalate based compounds, phthalate or terephthalate may be used, and more specifically, dioctyl terephthalate (DOTP) may be used.

And, the phthalate based compound may have purity of about 99% or more, preferably about 99.5% or more, more preferably about 98% or more, but it is not limited thereto, and phthalate based compounds having commercially available qualities and purities may be used.

The hydrogenation process of the phthalate based compound may be conducted in a liquid phase or gas phase, but in the present disclosure, the phthalate based compound is included in liquid-phase raw material, hydrogen is included in gas-phase raw material, and they are introduced into a reactor filled with a hydrogenation catalyst.

Specifically, in the hydrogenation process according to one embodiment of the invention, HAZE value of the liquid-phase raw material comprising a phthalate based compound, introduced into a reactor, is 8% or less, preferably 6% or less, more preferably 4% or less.

In general, light is diffused by diffusant on the internal or external surface of material through which light is transmitted, wherein wide-angle diffusion is referred to as HAZE, and the HAZE value is the numerical value of phenomenon visible to the naked eye. The HAZE value of liquid-phase raw material is influenced by salts or other ingredients existing in the liquid-phase raw material, and with increase in the content thereof, HAZE value of the liquid-phase raw material also increases. The salt means TPA-Na or MOTP-Na, but it is not limited thereto.

If the HAZE value of the liquid-phase raw material is greater than 8%, neutralized salt, and the like may exist in the liquid-phase raw material, and such impurities may poison a catalyst or generate acidic material by hydrogenation. Specifically, in a reactor, salt ingredients existing in the reactant react with hydrogen to produce acidic material, and thereby, not only acid value of the product may increase, but also catalytic activity may be deteriorated. Thus, in the present disclosure, by controlling the content of impurities in the reactants below a certain level, catalyst life may be improved as much as possible, and acid value of the product may be controlled low.

In the present disclosure, HAZE value of the liquid-phase raw material may be measured by HAZE measuring device such as haze-gard plus from BYK. Specifically, after filling about 100 ml of a sample in a Glass Cell from Hunter Lab having a path length of 50 mm, using the analysis apparatus of the following conditions, Haze value is measured 2-3 times repeatedly, and the average value is indicated:

<Analysis Apparatus Conditions>

Measuring Range: Haze 0-100%

Display resolution: 0.01 unit in range 0.00-9.99, 0.1 unit in range 10.0-99.9

Repeatability: ±0.1 unit

Reproducibility: ±0.4 unit

Meanwhile, in the present disclosure, a method for controlling HAZE value of the liquid-phase raw material introduced into the reactor for hydrogenation is not specifically limited. Specifically, the HAZE value of the liquid-phase raw material may be controlled within the above range, by filtering the liquid-phase raw material in a predetermined temperature range using a filter.

The filtering temperature may be 150° C. or less, preferably 120° C. or less. When filtering under the above temperature condition, salts and other ingredient existing in the liquid-phase raw material may be filtered, and HAZE value of the liquid-phase raw material may fulfill the above range. If the temperature is greater than 150° C., the salts and other ingredients may pass through a filter together with a phthalate based compound such as DOTP, and thus, the effect of decreasing the HAZE value of the liquid-phase raw material cannot be obtained. Meanwhile, although the filtering temperature is not specifically limited, considering filtering efficiency, it may be 80° C. or more, or 90° C. or more.

And, the filtering pressure may be greater than 1 bar, or 1.2 bar or more, or 1.5 bar or more, or 2 bar or more, and 4 bar or less, or 3.5 bar or less, or 3 bar or less. When simultaneously fulfilling the above temperature and pressure conditions, filtering efficiency may be further increased, and thus, the HAZE value of the liquid-phase raw material may be further decreased.

And, in order to realize the above HAZE value of the liquid-phase raw material, one or more of a neutralization agent and water may be additionally introduced into the liquid-phase raw material, before filtering.

Commonly, in a phthalate based compound or liquid-phase raw material comprising the same, impurities generated during the synthesis process of a phthalate based compound, such as diester based compounds represented by methyl(2-ethylhexyl) terephthalate (MOTP), monoester based compounds, unreacted terephthalic acid (TPA), and a synthesis catalyst, and the like exist. Since most of diester based compounds, monoester compounds and unreacted terephthalic acid have acidic properties, in case a neutralization agent is introduced in the liquid-phase raw material, the neutralization agent may react with the above compounds and precipitated in the form of a salt such as TPA-Na or MOTP-Na. And, a synthesis catalyst such as tetra isopropyl titanate is used during synthesis of a phthalate based compound, however, the synthesis catalyst remaining in the liquid-phase raw material is hydrolyzed by water and precipitated in the form of solid inorganic oxide such as titanium dioxide ($TiO_2$). Thus, by removing the precipitated impurities through the subsequent filtering, the effect of removing impurities in the liquid-phase raw material may be further increased.

As the neutralization agent, inorganic base such as NaOH, KOH, $Na_2CO_3$, and the like may be used, and these neutralization agents may be used alone, or in combinations of two or more kinds.

And, the neutralization agent may be introduced in an amount of 0.1 to 5 wt %, or 0.5 to 3 wt %, based on the total weight of the liquid-phase raw material, and in case introduced within the above content range, more excellent impurity removal effect may be exhibited.

And, the water may be introduced in an amount of 0.1 to 5 wt %, or 0.5 to 3 wt %, based on the total weight of the liquid-phase raw material, and in case introduced within the above content range, more excellent impurity removal effect may be exhibited.

And, in order to increase impurity removal efficiency and decrease HAZE value of the liquid-phase raw material, before filtering, specifically before introducing a neutralization agent or water or after the introduction and before filtering, a process of stripping the liquid-phase raw material may be optionally further conducted.

Through the stripping process, volatile materials such as alcohol, existing in the liquid-phase raw material, may be removed, and thereby, odor generation due to remaining alcohol in the final product may be prevented.

The stripping process may be conducted by a common stripping method, except using the liquid-phase raw material. For example, the stripping process may be conducted using steam, or under inert gas atmosphere such as nitrogen, argon, and the like, so as to prevent oxidation of the phthalate based compound.

However, in case a stripping process is conducted using steam, and the stripping process temperature is greater than 250° C., reverse reactions may occur during the stripping process, thus generating MOTP or TPA, and the like. These compounds may further increase haze or acid value of the liquid-phase raw material. Even if the liquid-phase raw material having increased haze or acid value is neutralized, salts in the liquid-phase raw material may increase during the neutralization process, and thereby, haze of the liquid-phase raw material fed to a hydrogenation reactor may also increase. As the result, not only lifespan of the hydrogenation catalyst may be shortened, but also acid value of the hydrogenated product may be further increased. During the stripping process, the reverse reaction speed by steam increases as the temperature is higher. Thus, in case the stripping process is conducted, particularly using steam, it may be preferable that the process is conducted at a temperature of 250° C. or less, or 120 to 250° C., and under relative pressure of −1.0 to −0.5 barg.

Meanwhile, in case stripping is conducted under nitrogen atmosphere, a reverse reaction does not occur regardless of a temperature, and thus, there is no concern about increase in salt content due to a neutralization agent and generation of MOTP, and the like. Thus, it may be more preferable that stripping is conducted under nitrogen atmosphere.

Meanwhile, in the hydrogenation process of a phthalate based compound according to one embodiment of the invention, the hydrogen as gas-phase raw material for hydrogenation may be introduced in an amount of 3 moles or more, or 4 moles or more, or 7 moles or more, and 300 moles or less, or 100 moles or less, or 50 moles or less, or 30 moles or less, based on 1 mole of the phthalate based compound in the liquid-phase raw material. If the amount of hydrogen is less than 3 moles based on 1 mole of the phthalate based compound, there is a concern about deterioration of reactivity, and if it is greater than 300 moles, the sizes of a reactor, gas phase process equipment of latter stage, instrumentation, and the like may excessively increased, thus increasing facility cost. Thus, the amount of hydrogen is preferably within the above range.

And, the hydrogenation is conducted in the presence of a hydrogenation catalyst. The hydrogenation catalyst may comprise transition metal as an active ingredient, and preferably, it may comprise one or more selected from the group consisting of ruthenium (Ru), palladium (Pd), rhodium (Rh) and platinum (Pt).

The hydrogenation catalyst may be used while supported in a carrier, wherein as the carrier, those known in the art may be used without limitations. Specifically, one or more carriers such as zirconia ($ZrO_2$), titania ($TiO_2$), alumina ($Al_2O_3$), silica ($SiO_2$), and the like may be used.

In case the hydrogenation catalyst is supported in a carrier, the amount of the active ingredient of the hydrogenation catalyst may be preferably 3 parts by weight or less, 2 parts by weight or less, or 1 part by weight or less, and 0.1 parts by weight or more, or 0.3 parts by weight or more, based on 100 parts by weight of the carrier. If the amount of the hydrogenation catalyst is greater than 3 parts by weight, based on 100 parts by weight of the carrier, reactions may rapidly progress on the catalyst surface, and during the process, side reactions may also increase, thus rapidly increasing the amount of by-products, and if it is less than 0.1 parts by weight, due to insufficient catalyst amount, yield of hydrogenation may decrease. Thus, the above range is preferable.

In the present disclosure, hydrogenation conditions are not specifically limited, but for example, the reaction pressure may be 50 bar or more, or 100 bar or more, or 110 bar or more, and 220 bar or less, or 200 bar or less, or 180 bar or less. If the reaction pressure is less than 50 bar, reactions may not sufficiently occur, and thus, an excessive amount of catalyst may be consumed, and residence time may too lengthen, thereby causing many problems such as by-products increase and acid value increase, and the like, and if it is greater than 220 bar, excessive electric power may be required during process operation, and production cost of equipment such as a reactor may significantly increase, and thus, the above range is preferable.

And, the reaction temperature may be 100° C. or more, or 120° C. or more, or 130° C. or more, and 300° C. or less, or 250° C. or less, or 200° C. or less. If the reaction temperature is less than 100° C., reaction speed may be too slow, and thus, reactions may not smoothly occur, and if it is greater than 300° C., by-products may rapidly increase, thus significantly increasing acid value of the product, and influencing catalyst life, and thus, the above range is preferable.

By such hydrogenation, the aromatic ring in the phthalate based compound is hydrogenated, thus converting into corresponding cyclohexane dicarboxylate.

After the reaction is finished, liquid hydrogenation product and gas-phase unreacted raw material are separated. The separated gas-phase raw material may be recycled to a hydrogenation process. And, recovered hydrogenation product may be finally separated through pressure reduction and cooling processes.

The hydrogenation product prepared and separated through the above hydrogenation process, namely, a hydrogenated phthalate based compound has acid value of 0.3 KOHmg/g or less, or 0.15 KOHmg/g or less, or 0.07 KOHmg/g or less. The lower the acid value of the hydrogenation product, more excellent the product quality, and thus, the lower limit is not limited, but for example, it may be 0.01 KOHmg/g or more, or 0.03 KOHmg/g or more. Wherein, the acid value range suggested above does not mean heating acid value. The acid value is the weight (mg) of potassium hydroxide (KOH) required to neutralize acid contained in 1 g of a sample, and it may be calculated by titration of a sample solution with 0.1N alcoholic KOH solution.

And, the hydrogenation product may have acid value after heating of 0.4 KOHmg/g or less, 0.25 KOHmg/g or less, or 0.15 KOHmg/g or less. The lower the acid value after heating, more excellent the product quality, and thus, the lower limit is not limited, but for example, it may be 0.01 KOHmg/g or more, 0.05 KOHmg/g or more, or 0.1 KOHmg/g or more.

Wherein, the acid value after heating of the hydrogenation product is a value obtained by titration and calculation by the same method as the above acid value measurement, after maintaining the hydrogenation product prepared and separated through the hydrogenation process of the invention, at 125° C. for 3 hours.

According to the hydrogenation process of the invention wherein liquid-phase raw material is introduced while controlling the HAZE value of the liquid-phase raw material, side reactions other than hydrogenation are inhibited, and thus, the amount of by-products is reduced, and the hydrogenation product exhibits low acid value as explained above, thereby obtaining high purity and high quality product.

FIG. 1 is a schematic diagram showing hydrogenation apparatus used for the hydrogenation process of the invention.

Referring to FIG. 1, the hydrogenation apparatus may consist of heat exchangers (a, b), a reactor (c) and a gas-liquid separator (d), and the like.

The heat exchangers (a, b) perform a function for raising temperature before gas-phase raw material (1) and liquid-phase raw material (3) are introduced into the reactor (c), and it can be omitted as necessary.

Temperature-raised gas-phase raw material (2) and liquid-phase raw material (4) are introduced into a tubular reactor (c) filled with a hydrogenation catalyst inside, and hydrogenation is progressed. The reactor may further comprise an external jacket for controlling heat in order to control reaction heat. Wherein, the temperature-raised gas-phase raw material (2) may be fed from the upper or lower part of the reactor, and the temperature-raised liquid-phase raw material (4) may be fed from the upper part of the reactor.

A reaction mixture (5) discharged from the reactor (c) is transferred to the gas-liquid separator (d), where a liquid reaction product (7) and gas-phase unreacted material (6) are separated. The separated reaction product (7) may be recovered and passed through additional purification operation, and the gas-phase unreacted material (6) may be discharged or recycled for reuse.

However, in FIG. 1, the position of each device may be changed, and other devices not shown in FIG. 1 may be included as necessary, and thus, the hydrogenation process of the invention is not limited to the apparatus and process sequence as shown in FIG. 1.

According to the above-explained hydrogenation process of the invention, acid value of the hydrogenation product may be controlled low, catalytic activity may be improved, and catalyst life may be prolonged, thereby improving the quality of the product and increasing economical efficiency of industrial process.

Thus, the hydrogenation product prepared by the above process, namely hydrogenated phthalate based compound may be usefully used as a plasticizer. Specifically, a plasticizer comprising the phthalate based compound may be used in products such as a stabilizer, paint, ink, liquid blowing agent (Masterbatch type), adhesive, and the like. Wherein, the phthalate based compound is as explained above, and more specifically, it may be phthalate or terephthalate.

And, since the hydrogenated phthalate based compound prepared according to the invention has excellent purity and low acid value, it has excellent quality as a plasticizer. Thus, it may be suitably used as a plasticizer of resin selected from ethylene vinylacetate, polyethylene, polypropylene, polyvinyl chloride, polystyrene, polyurethane, polybutadiene, silicon, thermoplastic elastomer, or copolymers thereof.

A resin composition comprising the phthalate based compound prepared according to the invention as a plasticizer, and comprising the above resin may be used for various products. For example, it may be used for manufacture of food packaging films (for example, wrap), industrial films, compound, deco sheets, deco tiles, soft sheets, hard sheets, electric wire and cable, wallpaper, foam mats, artificial leather, flooring, tarpaulin, glove, sealant, refrigerator gasket, hose, medical device, geogrid, mesh tarpaulin, toys, stationery, insulation tape, cloth coating, PVC labels for clothes or stationery, stopper liner, industrial or other stoppers, artificial bait, electronic equipment part (for example, sleeve), automobile interior material, adhesive, coating, and the like, but is not limited thereto.

Hereinafter, the actions and effects of the invention will be explained in more detail, through specific examples of the invention. However, these examples are presented only as the illustrations of the invention, and the scope of the right of the invention is not determined thereby.

<Preparation of Liquid-Phase Raw Material>

Preparation Example 1

To dioctyl terephthalate (DOTP), 15 wt % NaOH aqueous solution was introduced as a neutralization agent in an amount corresponding to 1 wt % of NaOH based on the total weight of the liquid-phase raw material, and water was introduced in an amount of 1 wt % based the total weight of the liquid-phase raw material, and then, nitrogen stripping was conducted, and filtering was conducted under filter operation conditions of 2 bar and 90~100° C. to prepare liquid-phase raw material.

Preparation Example 2

To dioctyl terephthalate (DOTP), 15 wt % NaOH aqueous solution was introduced as a neutralization agent in an amount corresponding to 1 wt % of NaOH based on the total weight of the liquid-phase raw material, and water was introduced in an amount of 1 wt % based the total weight of the liquid-phase raw material, and then, nitrogen stripping was conducted, and filtering was conducted under filter operation conditions of 2 bar and 100~120° C. to prepare liquid-phase raw material.

Preparation Example 3

To dioctyl terephthalate (DOTP), 15 wt % NaOH aqueous solution was introduced as a neutralization agent in an amount corresponding to 1 wt % of NaOH based on the total weight of the liquid-phase raw material, and water was introduced in an amount of 1 wt % based the total weight of the liquid-phase raw material, and then, nitrogen stripping was conducted, and filtering was conducted under filter operation conditions of 2 bar and 160~170° C. to prepare liquid-phase raw material.

Preparation Example 4

To dioctyl terephthalate (DOTP), 15 wt % NaOH aqueous solution was introduced as a neutralization agent in an amount corresponding to 0.5 wt % of NaOH based on the total weight of the liquid-phase raw material, and water was introduced in an amount of 0.5 wt % based the total weight of the liquid-phase raw material, and then, nitrogen stripping was conducted, and filtering was conducted under filter operation conditions of 2 bar and 160~170° C. to prepare liquid-phase raw material.

Experimental Example 1

Haze values of the liquid-phase raw materials prepared in Preparation Examples 1 to 4 were measured.

Specifically, in a Glass Cell from Hunter Lab having a path length of 50 mm, about 100 ml of each liquid-phase raw material prepared in Preparation Examples 1 to 4 was filled, and then, using haze-gard plus from BYK as HAZE measuring device, HAZE value was measured 2-3 times repeatedly, and the average value was shown in the following Table 1.

<Analysis Apparatus Conditions>

Measuring Range: Haze 0-100%

Display resolution: 0.01 unit in range 0.00-9.99, 0.1 unit in range 10.0-99.9

Repeatability: ±0.1 unit

Reproducibility: ±0.4 unit

TABLE 1

| | HAZE value (%) |
|---|---|
| Preparation Example 1 | 3.0 |
| Preparation Example 2 | 5.2 |
| Preparation Example 3 | 10.2 |
| Preparation Example 4 | 14.5 |

<Hydrogenation Process of Phthalate Based Compound>

Example 1

The liquid-phase raw material prepared in Preparation Example 1, and hydrogen as gas-phase raw material were respectively introduced into the reactor as shown in FIG. 1, and hydrogenation was conducted at a reaction temperature of 150° C. and reaction pressure of 110 bar.

Wherein, the mass flow rate of the liquid-phase raw material was 9.6 kg/hr, and hydrogen was introduced such that the mole ratio of hydrogen/DOTP became 10 moles. And, the volume flow rate of hydrogen and DOTP was 5:1, hydrogen introduction temperature was 140° C. and pressure was 150 bar, and DOTP introduction temperature was 140° C. and pressure was 150 bar.

The reactor was a single tubular type, the total length of the part in which a catalyst was filled in the tube was 3.0 m, and hydrogenation was conducted without an external jacket for controlling heat.

Wherein, the catalyst used in the reactor was supported ruthenium (Ru) catalyst (0.5 parts by weight of ruthenium, based on 100 parts by weight of silica carrier), and as the reactor, a cylindrical reactor with a diameter of 3 mm and a height of 3 mm was used.

Example 2

Hydrogenation was conducted by the same method as Example 1, except that the liquid-phase raw material prepared in Preparation Example 2 was used.

Comparative Example 1

Hydrogenation was conducted by the same method as Example 1, except that the liquid-phase raw material prepared in Preparation Example 3 was used.

Comparative Example 2

Hydrogenation was conducted by the same method as Example 1, except that the liquid-phase raw material prepared in Preparation Example 4 was used.

Experimental Example 2

For the hydrogenation of Examples 1, 2 and Comparative Examples 1, 2, initial conversion rate and conversion rate at the operation time of 48 hours, acid value of the hydrogenation product, acid value after heating of the hydrogenation product, and catalyst life were evaluated.

(1) Initial Conversion Rate:

From the amount of DOTP introduced at the beginning of the reaction, and the amount of DEHCH (di(2-ethylhexyl) cyclohexan-1,4-dicarboxylate) finally prepared, initial conversion rate was calculated according to the following Mathematical Formula 1.

Initial conversion rate=[(amount of finally prepared DEHCH)/(amount of DOTP introduced at the beginning of reaction))]×100 [Mathematical Formula 1]

(2) Conversion Rate at the Hydrogenation Apparatus Operation Time of 48 Hours:

From the amount of DOTP introduced at the beginning of the reaction, and the amount of DETCH prepared after hydrogenation apparatus operation time of 48 hours, conversion rate at the operation time of 48 hours was calculated according to the following Mathematical Formula 2.

Conversion rate at the hydrogenation apparatus operation time of 48 hours=[(amount of DETCH prepared after hydrogenation apparatus operation time of 48 hours)/(amount of DOTP introduced at the beginning of the reaction)]×100 [Mathematical Formula 2]

(3) Acid Value of Hydrogenation Product

After titration of the hydrogenation product obtained by separating gas-phase unreacted raw material from the reaction mixture with KOH reagent, the acid value was calculated according to the following Mathematical Formula 3.

$$\text{Acid value} = \frac{0.561 \times \alpha \times \beta}{\delta} \quad \text{[Mathematical Formula 3]}$$

(in the Mathematical Formula 3, α is the consumption amount of titration reagent (KOH), and β is 1.00, and δ is the amount of a sample (hydrogenation product) introduced)

(4) Acid Value of Hydrogenation Product after Heating:

After maintaining the hydrogenation product separated from the reaction mixture at 125° C. for 3 hours, it was titrated and the acid value after heating was calculated by the same method as the acid value measurement of the hydrogenation product.

(5) Catalyst Life:

Using the initial conversion rate ($X_0$) and conversion rate ($X_1$) at the hydrogenation apparatus operation time of 48 hours (2 days) calculated in (1) and (2), catalyst life was calculated according to the following Mathematical Formula 4.

$$\text{Catalyst life} = (X_0 - X_1)/X_0 \quad \text{[Mathematical Formula 4]}$$

The evaluation results were summarized in the following Table 2.

TABLE 2

| Experimental Example | | Example 1 | Example 2 | Comparative Example 1 | Comparative Example 2 |
|---|---|---|---|---|---|
| Kind of liquid-phase raw material | | Preparation Example 1 | Preparation Example 2 | Preparation Example 3 | Preparation Example 4 |
| HAZE value of liquid-phase raw material(%) | | 3.0 | 5.2 | 10.2 | 14.5 |
| Initial conversion rate | % | 75 | 75 | 75 | 75 |
| Conversion rate at the operation time of 48 hours | % | 73.8 | 73.4 | 68.2 | 62.2 |
| Conversion rate decrease(initial conversion rate − conversion rate at the operation time of 48 hours) | % | 1.2 | 1.6 | 6.8 | 12.8 |
| Acid value of hydrogenation product | KOHmg/g | 0.07 | 0.14 | 0.25 | 0.35 |
| Acid value of hydrogenation product after heating | KOHmg/g | 0.11 | 0.18 | 0.34 | 0.45 |
| Catalyst life | $(X_0 - X_1)/X_0$ | 1.6 | 2.1 | 9.1 | 17.1 |

Referring to Table 1, in the case of Examples 1 and 2 wherein hydrogenation was conducted by the hydrogen process according to the present disclosure, due to the use of liquid-phase raw material having low HAZE value, compared to Comparative Examples 1 and 2, decrease in conversion rate was small, acid value and acid value after heating of the final product also significantly decreased, and catalyst life was also improved.

The invention claimed is:

1. A process for hydrogenation of a phthalate based compound comprising steps of introducing gas-phase raw material comprising hydrogen; and liquid-phase raw material comprising a phthalate based compound and having a HAZE value of 6% or less into a reactor, and conducting hydrogenation of the hydrogen and phthalate based compound in the presence of a hydrogenation catalyst, wherein the process for hydrogenation further comprises a step of filtering at a temperature condition of 90° C. to 120° C. using a filter, before introducing the liquid raw material comprising a phthalate based compound and having a HAZE value of 6% or less; a step of introducing a neutralization agent and water and mixing them, before the filtering; and a step of stripping under a nitrogen atmosphere, after the introduction of the neutralization agent and water and before filtering, wherein the neutralization agent is introduced in an amount of 0.5 to 3 wt %, based on the total weight of the liquid-phase raw material, the water is introduced in an amount of 0.5 to 3 wt %, based on the total weight of the liquid-phase raw material, and acid value of a hydrogenation product separated after the hydrogenation is 0.15 KOHmg/g or less.

2. The process for hydrogenation of a phthalate based compound according to claim 1, wherein HAZE value of the liquid-phase raw material is 4% or less.

3. The process for hydrogenation of a phthalate based compound according to claim 1, wherein acid value of the hydrogenation product is 0.07 KOHmg/g or less.

4. The process for hydrogenation of a phthalate based compound according to claim 1, wherein acid value of the hydrogenation product after heating, measured after maintaining the hydrogenation product at 125° C. for 3 hours, is 0.4 KOHmg/g or less.

5. The process for hydrogenation of a phthalate based compound according to claim 1, wherein acid value of the hydrogenation product after heating, measured after maintaining the hydrogenation product at 125° C. for 3 hours, is 0.25 KOHmg/g or less.

6. The process for hydrogenation of a phthalate based compound according to claim 1, wherein the hydrogen is introduced in an amount of 3 to 300 moles, based on 1 mole of the phthalate based compound.

7. The process for hydrogenation of a phthalate based compound according to claim 1, wherein the phthalate based compound comprises phthalate, terephthalate, isophthalate, or carboxylic acid derivatives or mixtures thereof.

8. The process for hydrogenation of a phthalate based compound according to claim 1, wherein the phthalate based compound is phthalate or terephthalate.

9. The process for hydrogenation of a phthalate based compound according to claim 1, wherein the gas-phase raw material is fed from an upper part or a lower part of the reactor, and the liquid-phase raw material is fed from the upper part of the reactor.

10. The process for hydrogenation of a phthalate based compound according to claim 1, wherein the hydrogenation catalyst comprises ruthenium, rhodium, palladium, platinum or a mixture thereof, as an active ingredient.

11. The process for hydrogenation of a phthalate based compound according to claim 10, wherein the hydrogenation catalyst further comprises a carrier, and the active ingredient is comprised in an amount of 3 parts by weight, based on 100 parts by weight of the carrier.

* * * * *